United States Patent
Nakashima et al.

(10) Patent No.: US 11,690,534 B2
(45) Date of Patent: Jul. 4, 2023

(54) GAIT EVALUATION APPARATUS, GAIT TRAINING SYSTEM, AND GAIT EVALUATION METHOD

(71) Applicant: TOYOTA JIDOSHA KABUSHIKI KAISHA, Toyota (JP)

(72) Inventors: Issei Nakashima, Toyota (JP); Masayuki Imaida, Ichinomiya (JP); Takeru Fukagawa, Chiryu (JP); Eiichi Saitoh, Nagoya (JP); Satoshi Hirano, Nagoya (JP); Shigeo Tanabe, Toyoake (JP); Hiroki Tanikawa, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 414 days.

(21) Appl. No.: 16/157,477

(22) Filed: Oct. 11, 2018

(65) Prior Publication Data
US 2019/0150792 A1    May 23, 2019

(30) Foreign Application Priority Data

Nov. 17, 2017    (JP) .................................. 2017-222283

(51) Int. Cl.
*A61B 5/11*      (2006.01)
*A61B 5/103*     (2006.01)
(Continued)

(52) U.S. Cl.
CPC ............ *A61B 5/112* (2013.01); *A61B 5/1038* (2013.01); *A61B 5/1122* (2013.01);
(Continued)

(58) Field of Classification Search
CPC ..... A61B 5/112; A61B 5/1038; A61B 5/1122; A61B 5/1128; A61B 2505/09;
(Continued)

(56) References Cited

U.S. PATENT DOCUMENTS 5,885,229 A * 3/1999 Yamato ................ A61B 5/1038
                                                    600/592
6,666,831 B1* 12/2003 Edgerton ........... A63B 69/0064
                                                    600/595
(Continued)

FOREIGN PATENT DOCUMENTS

CN    103536424 A    1/2014
CN    106466219 A    3/2017
(Continued)

OTHER PUBLICATIONS

Itoh, N., et al., "Quantitative assessment of circumduction, hip hiking, and forefoot contact gait using Lissajous figures", Japanese Journal of Comprehensive Rehabilitation Science, vol. 3, Jan. 16, 2013, XP055524620, pp. 78-84.

*Primary Examiner* — Alex M Valvis
*Assistant Examiner* — Yasmeen S Warsi
(74) *Attorney, Agent, or Firm* — Oblon, McClelland, Maier & Neustadt, L.L.P.

(57) ABSTRACT

A gait evaluation apparatus that evaluates a training gait of a paralyzed patient suffering from paralysis in a leg includes an acquisition unit configured to acquire a plurality of motion amounts of a paralyzed body portion according to a gait motion and an evaluation unit configured to evaluate that the gait motion is an abnormal gait in a case where at least one of the motion amounts acquired by the acquisition unit meets any one of a plurality of abnormal gait criteria set in advance. The abnormal gait criteria include at least two or more first criteria, which are criteria relevant to motion amounts of different parts of the paralyzed body portion, or at least two or more second criteria, which are criteria relevant to motion amounts of the same part of the paralyzed body portion in different directions.

5 Claims, 10 Drawing Sheets

(51) Int. Cl.
*A61H 1/02* (2006.01)
*A61H 3/00* (2006.01)
*A63B 21/00* (2006.01)
*A63B 22/02* (2006.01)
*A63B 24/00* (2006.01)
*A63B 71/06* (2006.01)
*A63B 22/00* (2006.01)

(52) U.S. Cl.
CPC .......... *A61B 5/1128* (2013.01); *A61H 1/0262* (2013.01); *A61H 3/008* (2013.01); *A63B 21/00178* (2013.01); *A63B 22/02* (2013.01); *A63B 24/0062* (2013.01); *A63B 24/0087* (2013.01); *A63B 71/0622* (2013.01); *A61B 5/1117* (2013.01); *A61B 2505/09* (2013.01); *A63B 2022/0094* (2013.01); *A63B 2024/0068* (2013.01); *A63B 2220/806* (2013.01)

(58) Field of Classification Search
CPC .... A61B 5/1117; A61H 1/0262; A61H 3/008; A63B 21/00178; A63B 22/02; A63B 24/0062; A63B 24/0087; A63B 71/0622; A63B 2022/0094; A63B 2024/0068; A63B 2220/806
See application file for complete search history.

(56) References Cited

U.S. PATENT DOCUMENTS

| | | | | |
|---|---|---|---|---|
| 9,974,478 | B1 * | 5/2018 | Brokaw | A61B 5/486 |
| 10,610,131 | B1 * | 4/2020 | Thompson | A61B 5/112 |
| 10,702,442 | B2 * | 7/2020 | Sankai | A61H 1/02 |
| 2007/0202478 | A1 * | 8/2007 | Al-Obaidi | A61B 5/1038 434/247 |
| 2007/0275830 | A1 | 11/2007 | Lee et al. | |
| 2008/0039756 | A1 * | 2/2008 | Thorsteinsson | A61F 5/0123 600/595 |
| 2008/0234113 | A1 * | 9/2008 | Einav | A61H 1/0237 482/66 |
| 2014/0343460 | A1 * | 11/2014 | Evans, III | A61B 5/112 600/595 |
| 2016/0279418 | A1 * | 9/2016 | Courtine | A61N 1/0551 |
| 2016/0331560 | A1 * | 11/2016 | Tong | A61H 1/024 |
| 2017/0202724 | A1 * | 7/2017 | De Rossi | A61H 3/00 |
| 2017/0243354 | A1 * | 8/2017 | Tafazzoli | A61B 5/7275 |
| 2017/0312579 | A1 | 11/2017 | Nakashima | |
| 2018/0078390 | A1 * | 3/2018 | Seo | A61H 1/024 |
| 2018/0140496 | A1 * | 5/2018 | Sankai | A61H 1/02 |
| 2018/0141206 | A1 * | 5/2018 | Bereziy | A61H 3/00 |

FOREIGN PATENT DOCUMENTS

| | | |
|---|---|---|
| CN | 106572816 A | 4/2017 |
| EP | 3 238 686 A1 | 11/2017 |
| JP | 2010-22439 | 2/2010 |
| JP | 2016-43115 A | 4/2016 |
| JP | 2016-140591 A | 8/2016 |
| JP | 2016-177459 | 10/2016 |
| JP | 2016-531681 | 10/2016 |
| JP | 2017-29686 | 2/2017 |
| KR | 10-2017-0030633 A | 3/2017 |
| KR | 10-2017-0123251 A | 11/2017 |
| WO | WO 2015/028283 A1 | 3/2015 |
| WO | WO 2016/084285 A1 | 6/2016 |

* cited by examiner

GAIT EVALUATION APPARATUS, GAIT TRAINING SYSTEM, AND GAIT EVALUATION METHOD

INCORPORATION BY REFERENCE

The disclosure of Japanese Patent Application No. 2017-222283 filed on Nov. 17, 2017 including the specification, drawings and abstract is incorporated herein by reference in its entirety.

BACKGROUND

1. Technical Field

The present disclosure relates to a gait evaluation apparatus, a gait training system, and a gait evaluation method.

2. Description of Related Art

In order to avoid falls or collisions by oneself or third parties, there is known a technique of attaching an articulated structure for detecting a movement state to a target person to detect the start of falling (for example, refer to Japanese Unexamined Patent Application Publication No. 2010-022439 (JP 2010-022439 A)).

SUMMARY

In a case where a patient suffering from paralysis in the leg does gait training as a rehabilitation, the patient will not be trained in a case where a gait training apparatus predicts a fall at the start of gait motion of the patient and performs an avoidance operation. For example, in a case where a paralyzed patient is made to do gait training while continuing the gait a plurality of cycles with the degree of freedom in the gait motion within a range in which the paralyzed patient does not completely fall down, the determination of an abnormal gait is very difficult unlike in the case of predicting a fall. For example, the gait of a paralyzed patient varies according to the disease. In addition, even in a case where the motion amount of a part involved in gait is similar to that of a healthy person, the gait of the paralyzed patient is often evaluated as an abnormal gait as observed as a whole.

The disclosure provides a gait evaluation apparatus, a gait training system, and a gait evaluation method for accurately evaluating an abnormal gait in gait training of a paralyzed patient suffering from paralysis in the leg.

A first aspect of the disclosure relates to a gait evaluation apparatus. The gait evaluation apparatus evaluates a training gait of a paralyzed patient suffering from paralysis in a leg. The gait evaluation apparatus includes an acquisition unit and an evaluation unit. The acquisition unit is configured to acquire a plurality of motion amounts of a paralyzed body portion, which includes an affected leg that is a leg suffering from paralysis, according to a gait motion. The evaluation unit is configured to evaluate that the gait motion is an abnormal gait in a case where at least one of the motion amounts acquired by the acquisition unit meets any one of a plurality of abnormal gait criteria set in advance. The abnormal gait criteria include at least two or more first criteria, which are criteria relevant to motion amounts of different parts of the paralyzed body portion, or at least two or more second criteria, which are criteria relevant to motion amounts of the same part of the paralyzed body portion in different directions. According to the first aspect of the disclosure, the motion amount is determined for a plurality of different types of abnormal gait criteria described above, and the gait motion is evaluated as an abnormal gait in a case where the motion amount meets any one of the abnormal gait criteria. Therefore, for various gaits of a paralyzed patient who does gait training while continuing the gait a plurality of cycles with the degree of freedom in the gait motion, any abnormal gait can be correctly evaluated.

In the gait evaluation apparatus according to the first aspect of the disclosure, the paralyzed patient may be a hemiplegic patient suffering from paralysis in one leg. The evaluation unit may evaluate the abnormal gait for at least one of each step of the affected leg or one cycle including one step of the affected leg and one step of a healthy leg not suffering from paralysis. According to the first aspect of the disclosure, the patient or the assistant can be notified of the situation in more real time by performing the evaluation in the cycle described above. In addition, the control of auxiliary operation or the like in the gait training apparatus can be successively changed as needed.

In the gait evaluation apparatus according to the first aspect of the disclosure, the first criteria may be selected from a criterion relevant to a motion amount of a trunk, a criterion relevant to a motion amount of a knee joint, and a criterion relevant to a motion amount of a foot portion from an ankle. According to the first aspect of the disclosure, more appropriate gait evaluation can be performed by performing the selection as described above.

In the gait evaluation apparatus according to the first aspect of the disclosure, the second criteria may include a criterion relevant to a motion amount of the trunk in a gait direction and a criterion relevant to a motion amount of the trunk in an orthogonal direction perpendicular to the gait direction. According to the first aspect of the disclosure, more appropriate gait evaluation can be performed by the combination described above.

In the gait evaluation apparatus according to the first aspect of the disclosure, the abnormal gait criteria may be set to different criteria in a swing phase and a stance phase of the affected leg. According to the first aspect of the disclosure, the gait evaluation can be performed more accurately by performing the setting as described above.

A second aspect of the disclosure relates to a gait training system including the gait evaluation apparatus described above and a gait assistance device. The gait assistance device is attached to the affected leg. The gait assistance device has a plurality of sensors configured to acquire the motion amounts according to the gait motion. According to the second aspect of the disclosure, since the gait assistance device attached to the affected leg includes the sensors configured to acquire the motion amounts, the motion amount according to a gait motion can be acquired more directly.

The gait training system according to the second aspect of the disclosure may further include a treadmill and a falling prevention device. The treadmill serves as a gait surface on which the paralyzed patient walks. The falling prevention device is configured to prevent the paralyzed patient from falling on the treadmill. The evaluation unit may evaluate the abnormal gait for a trial in which the paralyzed patient continuously walks on the treadmill. According to the second aspect of the disclosure, the gait evaluation can be appropriately performed for the continuous gait training by adopting the configuration described above.

The gait training system according to the second aspect of the disclosure may further include a presentation unit configured to present information regarding an evaluation of the evaluation unit. According to the second aspect of the disclosure, since the patient can check the presentation of the information by the presentation unit, the patient can also try to change his or her gait during the course of a series of trainings.

In the gait training system according to the second aspect of the disclosure, the presentation unit may perform a single abnormality presentation even in a case where each of the motion amounts meets any one of the abnormal gait criteria. According to the second aspect of the disclosure, during the training, it is possible to prevent the patient from being confused by performing a simpler presentation.

A third aspect of the disclosure relates to a gait evaluation method for evaluating a training gait of a paralyzed patient suffering from paralysis in a leg. The gait evaluation method includes: acquiring a plurality of motion amounts of a paralyzed body portion, which includes an affected leg that is a leg suffering from paralysis, according to a gait motion; and evaluating that the gait motion is an abnormal gait in a case where at least one of the acquired motion amounts meets any one of a plurality of abnormal gait criteria set in advance. The abnormal gait criteria include at least two or more first criteria, which are criteria relevant to motion amounts of different parts of the paralyzed body portion, or at least two or more second criteria, which are criteria relevant to motion amounts of the same part of the paralyzed body portion in different directions. According to the third aspect of the disclosure, the motion amount is determined for a plurality of different types of abnormal gait criteria described above, and the gait motion is evaluated as an abnormal gait in a case where the motion amount meets any one of the abnormal gait criteria. Therefore, for various gaits of a paralyzed patient, any abnormal gait can be correctly evaluated.

According to the aspects of the disclosure, it is possible to provide a gait evaluation apparatus and the like for accurately evaluating an abnormal gait in gait training of a paralyzed patient suffering from paralysis in the leg.

BRIEF DESCRIPTION OF THE DRAWINGS

Features, advantages, and technical and industrial significance of exemplary embodiments will be described below with reference to the accompanying drawings, in which like numerals denote like elements, and wherein.

DETAILED DESCRIPTION OF EMBODIMENTS

Hereinafter, the disclosure will be described through embodiments.

Figure 1:
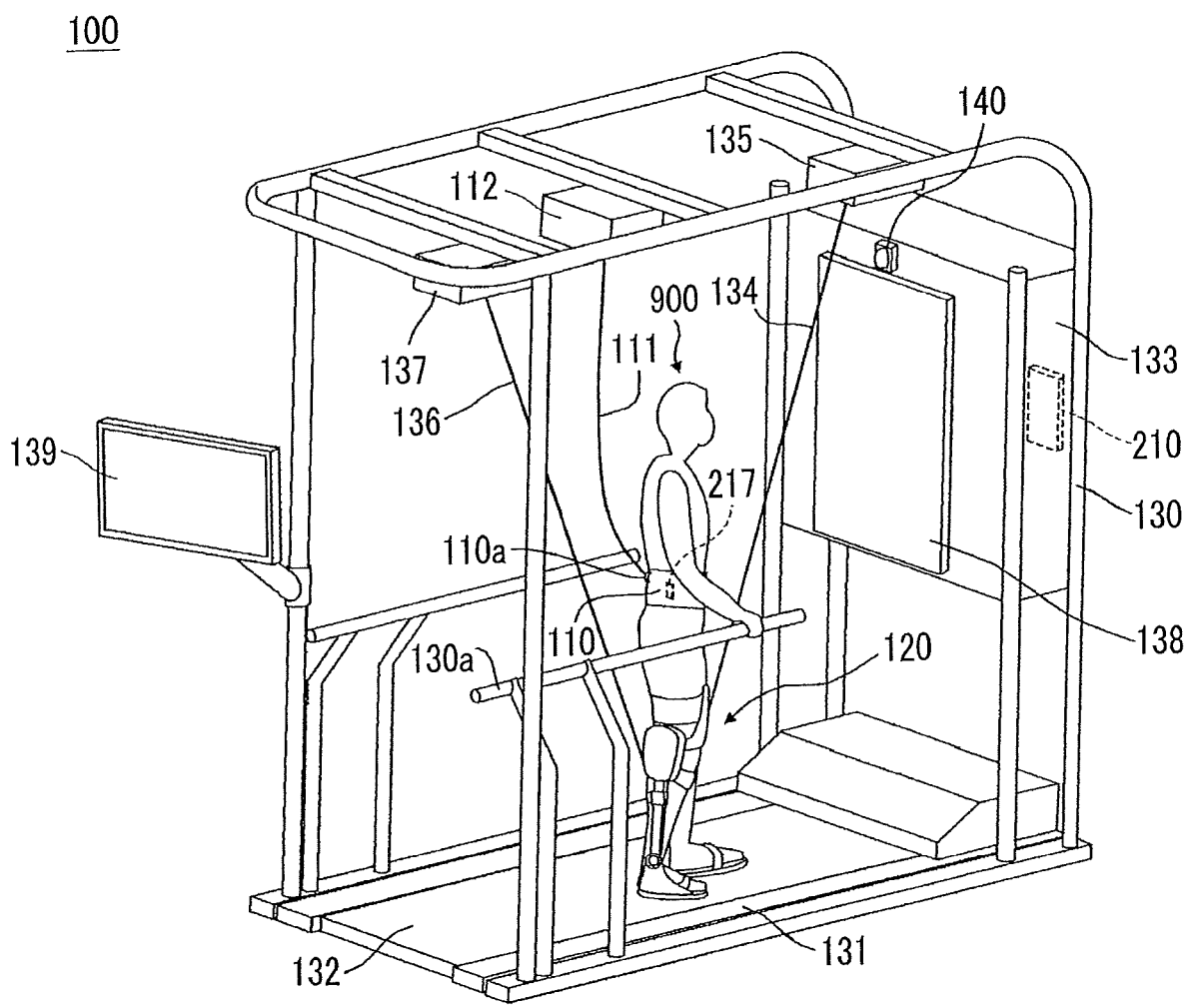
FIG. 1 is a schematic perspective view of a gait training apparatus according to the present embodiment.

FIG. 1 is a schematic perspective view of a gait training apparatus 100 according to the present embodiment. The gait training apparatus 100 is an apparatus for gait training of a trainee 900 who is a hemiplegic patient suffering from paralysis in one leg. The gait training apparatus 100 mainly includes a control panel 133 attached to a frame 130 forming the entire framework, a treadmill 131 on which the trainee 900 walks, and a gait assistance device 120 attached to an affected leg that is a leg portion on the paralyzed side of the trainee 900.

The frame 130 stands on the treadmill 131 installed on the floor surface. The treadmill 131 rotates a ring-shaped belt 132 with a motor (not shown). The treadmill 131 is a device that prompts the trainee 900 to walk. The trainee 900 who is to do gait training rides on the belt 132, and tries a gait motion according to the movement of the belt 132.

The frame 130 supports the control panel 133 in which an overall controller 210 for controlling a motor or a sensor is housed, a training monitor 138 (for example, a liquid crystal panel) for presenting the progress of training and the like to the trainee 900, and the like. The frame 130 supports a front side pulling unit 135 in the vicinity of the front side of the upper portion of the head of the trainee 900, a harness pulling unit 112 in the vicinity of the upper portion of the head of the trainee 900, and a rear side pulling unit 137 in the vicinity of the rear side of the upper portion of the head of the trainee 900. The frame 130 includes a handrail 130a for the trainee 900 to grasp.

A camera 140 functions as an imaging unit for observing the entire body of the trainee 900. The camera 140 is installed in the vicinity of the training monitor 138 so as to face the trainee 900. The camera 140 includes a set of a lens and an imaging element having an angle of view for imaging the entire body of the trainee 900. The imaging element is, for example, a complementary metal oxide semiconductor (CMOS) image sensor, and converts an optical image formed on the imaging surface into an image signal.

A first end of a front side wire 134 is connected to a winding mechanism of the front side pulling unit 135, and a second end of the front side wire 134 is connected to the gait assistance device 120. The winding mechanism of the front side pulling unit 135 winds or unwinds the front side wire 134 according to the movement of the affected leg by turning on and off a motor (not shown). A first end of a rear side wire 136 is connected to a winding mechanism of the rear side pulling unit 137, and a second end of the rear side wire 136 is connected to the gait assistance device 120. The winding mechanism of the rear side pulling unit 137 winds or unwinds the rear side wire 136 according to the movement of the affected leg by turning on and off a motor (not shown). By the cooperative operation of the front side pulling unit 135 and the rear side pulling unit 137 described above, the load of the gait assistance device 120 is canceled so that the load does not become a burden on the affected leg, and furthermore, the swinging motion of the affected leg is assisted depending on the degree of setting.

For example, an operator who is a training assistant sets a high assistance level for the trainee 900 who has severe paralysis. In a case where the high assistance level is set, the front side pulling unit 135 winds up the front side wire 134 with a relatively large force in accordance with the swing timing of the affected leg. As the training progresses and no assistance is needed, the operator sets the assistance level to the minimum. In a case where the assistance level is set to the minimum, the front side pulling unit 135 winds up the front side wire 134 with a force that cancels the own weight of the gait assistance device 120 in accordance with the swing timing of the affected leg.

The gait training apparatus 100 includes a falling prevention harness device as a safety device having a brace 110, the harness wire 111, and the harness pulling unit 112 as main components. The brace 110 is a belt wrapped around the abdomen of the trainee 900, and is fixed to the waist by a hook and loop fastener, for example. The brace 110 includes a connection hook 110a for connecting a first end of the harness wire 111 as a suspender. The trainee 900 attaches the brace 110 thereto so that the connection hook 110a is located at the back portion.

The first end of the harness wire 111 is connected to the connection hook 110a of the brace 110, and the second end of the harness wire 111 is connected to the winding mechanism of the harness pulling unit 112. The winding mechanism of the harness pulling unit 112 winds or unwinds the harness wire 111 by turning on and off a motor (not shown). Through the configuration described above, in a case where the trainee 900 is about to fall down, the fall prevention harness device prevents the falling of the trainee 900 by winding up the harness wire 111 according to the instruction of the overall controller 210 that detects the movement of the trainee 900 and supporting the upper body of the trainee 900 with the brace 110.

The brace 110 includes a posture sensor 217 for detecting the posture of the trainee 900. The posture sensor 217 is, for example, a combination of a gyro sensor and an acceleration sensor, and outputs an inclination angle of the abdomen to which the brace 110 is attached with respect to the direction of gravity.

A management monitor 139 is attached to the frame 130, and is a display input device mainly for the monitoring and operation of the operator. The management monitor 139 is, for example, a liquid crystal panel, and a touch panel is provided on the surface of the liquid crystal panel. The management monitor 139 presents various menu items relevant to the training setting, various parameter values at the time of training, a training result, and the like.

Figure 2:
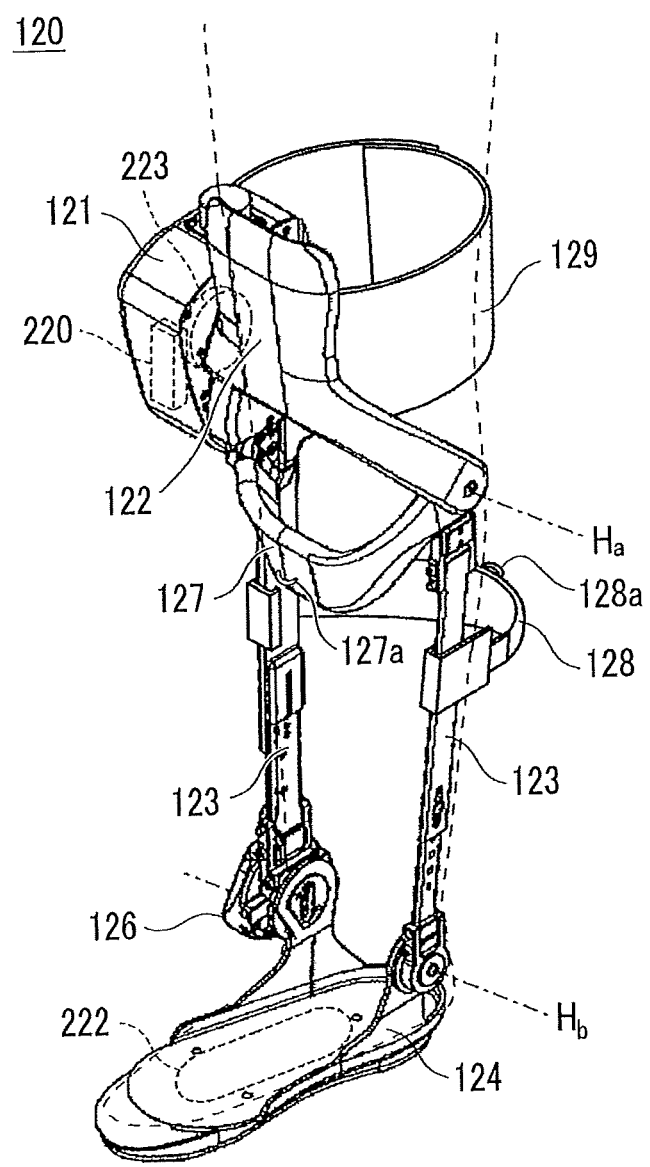
FIG. 2 is a schematic perspective view of a gait assistance device.

The gait assistance device 120 is attached to the affected leg of the trainee 900, and assists the gait of the trainee 900 by reducing the load of extension and bending in the knee joint of the affected leg. FIG. 2 is a schematic perspective view of the gait assistance device 120. The gait assistance device 120 mainly includes a controller 121, a plurality of frames for supporting respective parts of the affected leg, and a load sensor 222 for detecting a load applied to the sole.

The controller 121 includes an auxiliary controller 220 for controlling the gait assistance device 120, and includes a motor (not shown) for generating a driving force for assisting extension and bending movements of the knee joint. The frames for supporting respective parts of the affected leg include an upper leg frame 122, a lower leg frame 123 rotatably connected to the upper leg frame 122, a foot frame 124 rotatably connected to the lower leg frame 123, a front side connection frame 127 for connecting the front side wire 134, and a rear side connection frame 128 for connecting the rear side wire 136.

The upper leg frame 122 and the lower leg frame 123 relatively rotate around a hinge axis $H_a$ shown in the diagram. The motor of the controller 121 rotates according to the instruction of the auxiliary controller 220 to assist the upper leg frame 122 and the lower leg frame 123 to be relatively opened or closed around the hinge axis $H_a$. An angle sensor 223 housed in the controller 121 is, for example, a rotary encoder, and detects an angle formed by the upper leg frame 122 and the lower leg frame 123 around the hinge axis $H_a$. The lower leg frame 123 and the foot frame 124 relatively rotate around the hinge axis $H_b$ shown in the diagram. The angle range of relative rotation is adjusted in advance by an adjustment mechanism 126.

The front side connection frame 127 is provided so as to extend in the right and left direction of the front side of the upper leg and be connected to the upper leg frame 122 at both ends. In the front side connection frame 127, a connection hook 127a for connecting the front side wire 134 is provided in the vicinity of the center in the right and left direction. The rear side connection frame 128 is provided so as to extend in the right and left direction of the rear side of the lower leg and be connected to the lower leg frame 123, which extends up and down, at both ends. In the rear side connection frame 128, a connection hook 128a for connecting the rear side wire 136 is provided in the vicinity of the center in the right and left direction.

The upper leg frame 122 includes an upper leg belt 129. The upper leg belt 129 is a belt integrally provided in the upper leg frame, and is wrapped around the upper leg of the affected leg to fix the upper leg frame 122 to the upper leg. The fixation of the upper leg prevents the entire gait assistance device 120 from being displaced with respect to the leg portion of the trainee 900.

The load sensor 222 is a load sensor embedded in the foot frame 124. The load sensor 222 detects the magnitude and distribution of the vertical load applied to the sole of the trainee 900. The load sensor 222 is, for example, a resistance change detection type load detection sheet in which electrodes are arranged in a matrix.

Figure 3:
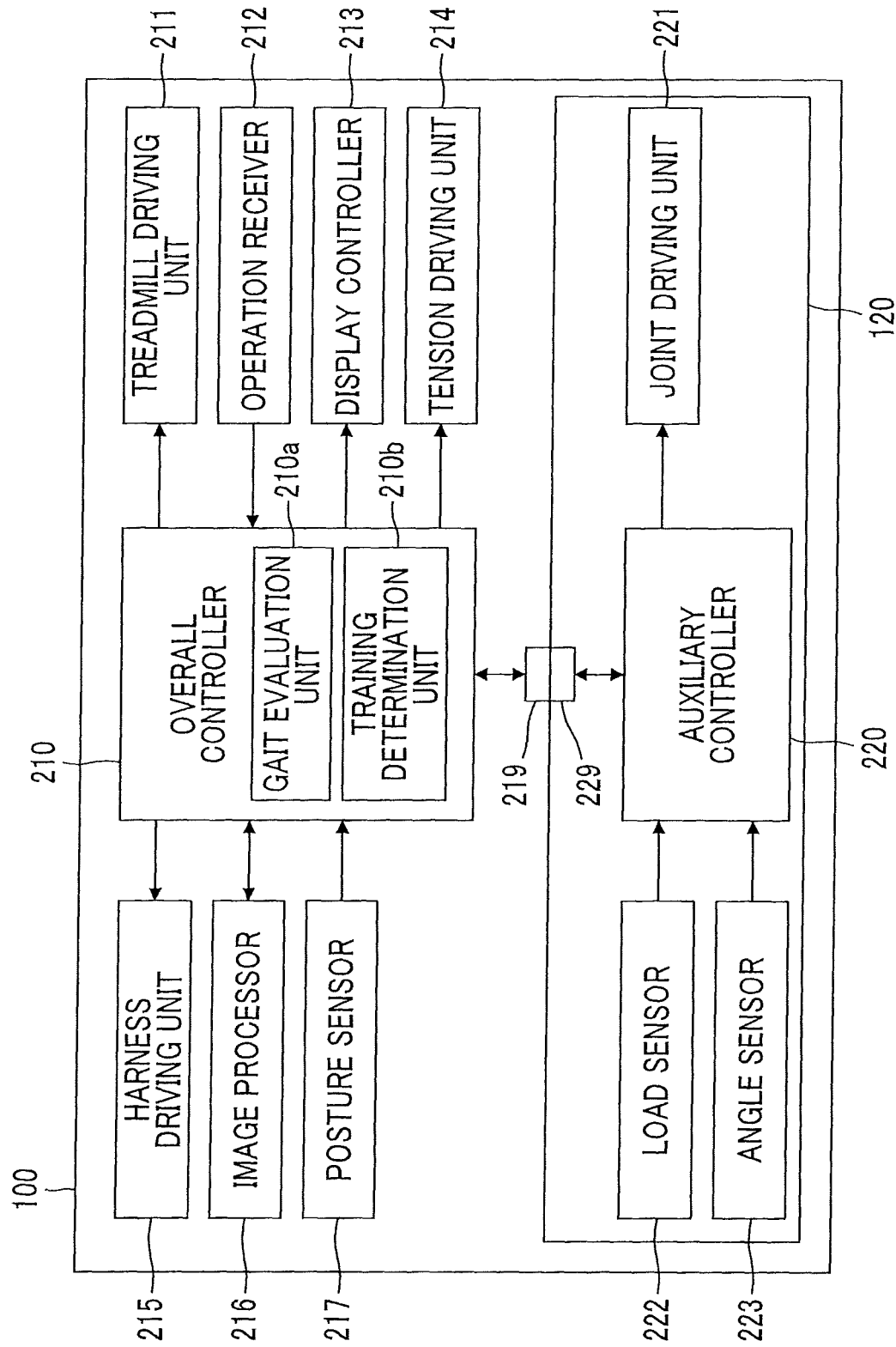
FIG. 3 is a diagram showing the system configuration of the gait training apparatus.

The system configuration of the gait training apparatus 100 will be described. FIG. 3 is a system configuration diagram of the gait training apparatus 100. The overall controller 210 is, for example, a microprocessor unit (MPU), and controls the entire apparatus by executing a control program read from a system memory. A treadmill driving unit 211 includes a motor for rotating the belt 132 and a motor driving circuit. The overall controller 210 controls the rotation of the belt 132 by transmitting a driving signal to the treadmill driving unit 211. For example, the rotation speed of the belt 132 is adjusted according to the gait speed set by the operator.

An operation receiver 212 receives an input operation from the trainee 900 or the operator, and transmits the operation signal to the overall controller 210. The trainee 900 or the operator gives an instruction to turn on or off the power supply or to start training or inputs numerical values relevant to setting or selects a menu item by operating operation buttons provided in the device, a touch panel superimposed on the management monitor 139, an attached remote controller, and the like, all of which form the operation receiver 212.

A display controller 213 receives the display signal from the overall controller 210, generates a display screen, and displays the display screen on the training monitor 138 or the management monitor 139. According to the display signal, the display controller 213 generates a screen showing the progress of the training or a real-time video captured by the camera 140.

A tension driving unit 214 includes a motor for pulling the front side wire 134 and a motor driving circuit, which form the front side pulling unit 135, and a motor for pulling the rear side wire 136 and a motor driving circuit, which form the rear side pulling unit 137. The overall controller 210 controls the winding of the front side wire 134 and the winding of the rear side wire 136 by transmitting a driving signal to the tension driving unit 214. Without being limited to the winding operation, the overall controller 210 controls the tensile force of each wire by controlling the driving torque of the motor. For example, the overall controller 210 assists the swinging motion of the affected leg by identifying a timing, at which the affected leg switches from the stance state to the swing state, based on the detection result of the load sensor 222 and increasing or decreasing the tensile force of each wire in synchronization with the timing.

A harness driving unit 215 includes a motor for pulling the harness wire 111 and a motor driving circuit, which form the harness pulling unit 112. The overall controller 210 controls the winding of the harness wire 111 and the tensile force of the harness wire 111 by transmitting a driving signal to the harness driving unit 215. For example, in a case where the falling of the trainee 900 is predicted, the overall controller 210 winds up the harness wire 111 by a certain amount to prevent the trainee 900 from falling.

According to the instruction from the overall controller 210, an image processor 216 performs image processing on the image signal received from the camera 140 to generate image data. According to the instruction from the overall controller 210, the image processor 216 can perform image processing on the image signal received from the camera 140 and execute specific image analysis. For example, the image processor 216 detects the position (stance position) of the foot of the affected leg in contact with the treadmill 131 by image analysis. Specifically, the stance position is calculated, for example, by extracting an image region in the vicinity of the distal end of the foot frame 124 and analyzing an identification marker drawn on the belt 132 overlapping the distal end.

The posture sensor 217 detects the above-described inclination angle of the abdomen of the trainee 900 with respect to the direction of gravity, and transmits the detection signal to the auxiliary controller 220. The overall controller 210 calculates the posture of the trainee 900, specifically, the inclination angle of the trunk by using the detection signal from the posture sensor 217. The overall controller 210 and the posture sensor 217 may be connected by wires or may be connected by short-range wireless communication.

The overall controller 210 also functions as a function execution unit that executes various kinds of control or calculations relevant to control. A gait evaluation unit 210a evaluates whether or not the gait motion of the trainee 900 is an abnormal gait using the acquired various kinds of sensor information. A training determination unit 210b determines a training result of a series of gait training based on the accumulated number of abnormal gaits evaluated by the gait evaluation unit 210a. Specific processing will be described later.

As described above, the gait assistance device 120 is attached to the affected leg of the trainee 900, and the gait training apparatus 100 includes a communication connection IF 219 connected to the overall controller 210 in order to send an instruction to the gait assistance device 120 or to receive sensor information. A communication connection IF 229 connected to the communication connection IF 219 by wired or wireless connection is provided in the gait assistance device 120. The communication connection IF 229 is connected to the auxiliary controller 220 of the gait assistance device 120. The communication connection IFs 219, 229 are communication interfaces conforming to the communication standard, for example, wireless local area networks (LANs).

The auxiliary controller 220 is, for example, an MPU, and controls the gait assistance device 120 by executing a control program given from the overall controller 210. The state of the gait assistance device 120 is transmitted to the overall controller 210 through the communication connection IFs 219, 229. In response to the instruction from the overall controller 210, the gait assistance device 120 is started or stopped.

A joint driving unit 221 includes a motor of the controller 121 and a motor driving circuit. The auxiliary controller 220 transmits a driving signal to the joint driving unit 221 to assist the upper leg frame 122 and the lower leg frame 123 to be relatively opened or closed around the hinge axis $H_a$. By the operation described above, the extension operation and the bending operation of the knee are assisted, or knee folding is prevented.

The load sensor 222 detects the above-described magnitude and distribution of the vertical load applied to the sole of the trainee 900, and transmits the detection signal to the auxiliary controller 220. The auxiliary controller 220 receives and analyzes the detection signal to determine a swing state or a stance state, perform switching estimation, and the like.

The angle sensor 223 detects the above-described angle formed by the upper leg frame 122 and the lower leg frame 123 around the hinge axis $H_a$, and transmits the detection signal to the auxiliary controller 220. The auxiliary controller 220 receives the detection signal, and calculates the opening angle of the knee joint.

The gait of a patient suffering from paralysis in the leg varies depending on a part or the extent of the disease. Accordingly, it is difficult to evaluate an abnormal gait, which is determined to have a higher possibility of falling, with one criterion. Focusing on the motion of a part of the leg, even a gait that is evaluated as an abnormal gait in a case where the gait is observed as a whole may be almost the same as the motion of normal gait. Therefore, the normal gait evaluation apparatus evaluates an abnormal gait as a normal gait in some cases.

In the embodiment of the present disclosure, there are at least seven classified patterns in abnormal gaits seen in hemiplegic patients. In a case where an abnormal gait criterion is set for each pattern, it can be seen that the gait motion of the trainee 900 can be evaluated as an abnormal gait in a case where the gait of the trainee 900 meets any abnormal gait criterion. In the gait training apparatus 100 according to the present embodiment, the gait evaluation unit 210a evaluates whether or not the gait motion of the trainee 900 is an abnormal gait by comparing the motion amount of each paralyzed body portion with each abnormal gait criterion. Hereinafter, each abnormal gait criterion and an abnormal gait evaluation method will be described.

Figure 4:
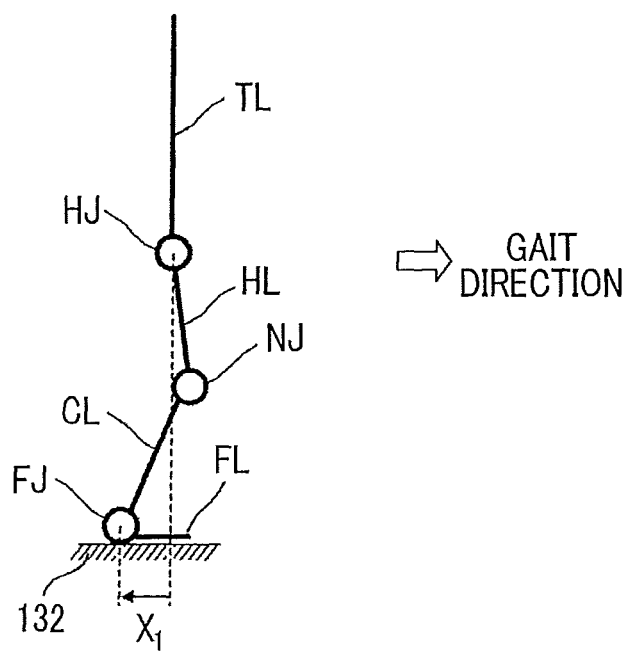
FIG. 4 is a diagram illustrating the first abnormal gait criterion.

FIG. 4 is a diagram illustrating the first abnormal gait criterion. FIG. 4 is a schematic diagram in a case where a paralyzed body portion, which is the lower body of the affected leg side, is observed from the side with respect to the gait direction, and shows a trunk TL, a hip joint HJ, a thigh HL, a knee joint NJ, a lower leg CL, a foot joint FJ, a foot FL from the top. In the present embodiment, "leg" and "leg portion" are used as terms indicating the entire lower part than the hip joint HJ, and "foot" and "foot portion" are used as terms indicating parts from the ankle to the toe.

In order to determine whether or not the gait of the trainee 900 meets the first abnormal gait criterion, the overall controller 210 detects, as a first motion amount according to the gait motion, a distance $X_1$ along the gait direction from the hip joint HJ to the foot joint FJ in a case where the affected leg has finished a swing phase and landed. In the normal gait of a healthy leg, the point of landing after the swing phase should be located ahead of the hip joint HJ in the gait direction. In the gait of the affected leg, the affected leg cannot be sufficiently moved to the front since the affected leg cannot be sufficiently swung. For this reason, the point of landing may be slightly ahead of the hip joint HJ, or may be behind the hip joint HJ.

"Less than a reference distance $X_{c1}$" is set as the first abnormal gait criterion. In a case where the distance $X_1$ detected in the gait motion is less than the reference distance $X_{c1}$, determination as an abnormal gait is made. The overall controller 210 acquires the detection signal from the load sensor 222 and the image data from the camera 140, and detects the distance $X_1$ at the end of the swing phase using the acquired information. For example, in a case where $X_{c1}$=20 cm (20 cm forward from the hip joint HJ) is set, the gait evaluation unit 210a evaluates the gait motion of the trainee 900 as an abnormal gait in a case where the detected distance $X_1$ is 10 cm or −5 cm. The reference distance $X_{c1}$ may be changed according to the physique of the trainee 900, the degree of progress of rehabilitation, and the like.

Figure 5:
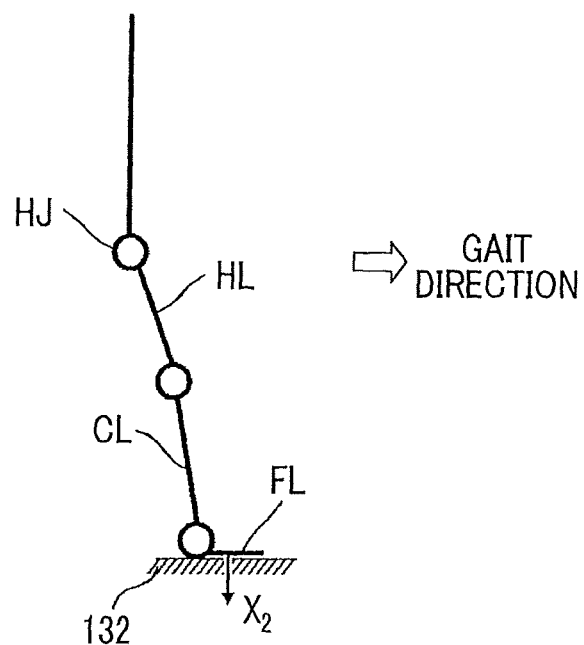
FIG. 5 is a diagram illustrating the second abnormal gait criterion.

FIG. 5 is a diagram illustrating the second abnormal gait criterion. FIG. 5 is a schematic diagram in a case where a paralyzed body portion, which is the lower body of the affected leg side, is observed from the side with respect to the gait direction, and shows each body portion in the same manner as in FIG. 4.

In order to determine whether or not the gait of the trainee 900 meets the second abnormal gait criterion, the overall controller 210 detects a sole load $X_2$ in the swing phase of the affected leg as a second motion amount according to the gait motion. In the normal gait of a healthy leg, the sole does not touch the ground in the swing phase. In the gait of the affected leg, there is not enough power to lift the entire leg. For this reason, so-called dragging gait may occur, such as pushing the leg forward with the sole in contact with the ground.

"Larger than a reference load $X_{c2}$" is set as the second abnormal gait criterion. In a case where the load $X_2$ detected in the gait motion is larger than the reference load $X_{c2}$, determination as an abnormal gait is made. The overall controller 210 acquires the detection signal from the load sensor 222 and the image data from the camera 140, and detects the load $X_2$ in the swing phase using the acquired information. Normally, $X_{c2}$=0 is set. In the swing phase, in a case where even a slight load from the sole is detected, the gait evaluation unit 210a evaluates the gait motion of the trainee 900 as an abnormal gait. The gait evaluation unit 210a may allow some ground contact according to the degree of progress of rehabilitation or the like. For example, $X_{c2}$=10N may be set. The gait evaluation unit 210a may use the accumulated load in the swing phase as a reference value.

Figure 6:
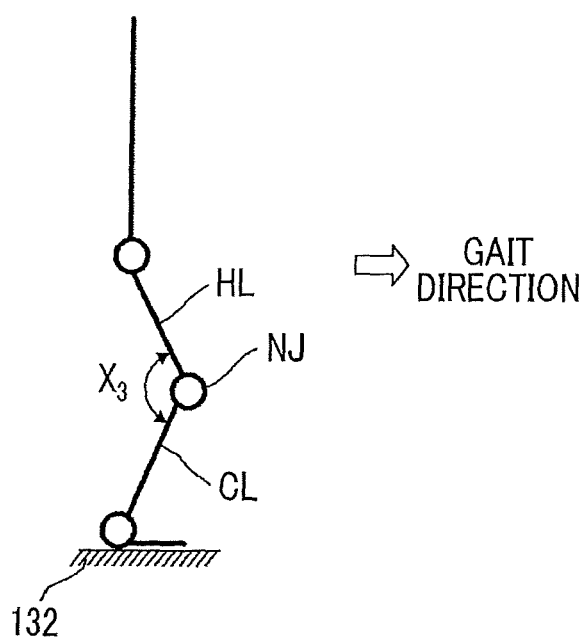
FIG. 6 is a diagram illustrating the third abnormal gait criterion.

FIG. 6 is a diagram illustrating the third abnormal gait criterion. FIG. 6 is a schematic diagram in a case where a paralyzed body portion, which is the lower body of the affected leg side, is observed from the side with respect to the gait direction, and shows each body portion in the same manner as in FIG. 4.

In order to determine whether or not the gait of the trainee 900 meets the third abnormal gait criterion, the overall controller 210 detects a bending angle $X_3$ of the knee joint NJ during the stance of the affected leg as a third motion amount according to the gait motion. In the normal gait of a healthy leg, the knee joint NJ during the stance does not bend so much. In the gait of the affected leg, the knee joint NJ may bend greatly during the stance since the power of the knee joint NJ to support the upper body is not sufficient. In some cases, so-called knee folding occurs.

"Less than a reference angle $X_{c3}$" is set as the third abnormal gait criterion. In a case where the bending angle $X_3$ detected in the gait motion is smaller than the reference angle $X_{c3}$, determination as an abnormal gait is made. The overall controller 210 acquires the detection signal from the angle sensor 223 and the image data from the camera 140, and detects the bending angle $X_3$ during the stance using the acquired information. For example, in a case where $X_{c3}$=165° is set, the gait evaluation unit 210a evaluates the gait motion of the trainee 900 as an abnormal gait in a case where the detected bending angle $X_3$ is 140°. The gait evaluation unit 210a evaluates the gait motion of the trainee 900 as an abnormal gait in a case where the bending angle $X_3$ continuously detected during the stance is less than the reference angle $X_{c3}$ at least once. The reference angle $X_{c3}$ may be changed according to the age of the trainee 900, the degree of progress of rehabilitation, and the like.

Figure 7:
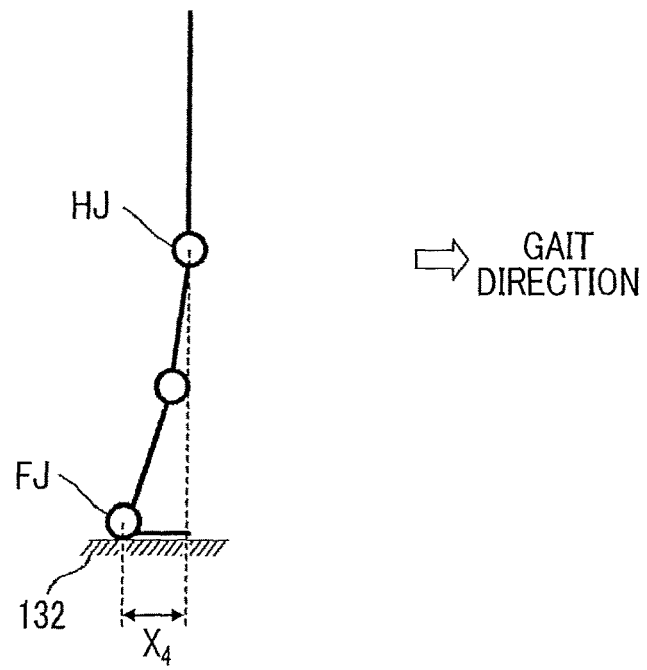
FIG. 7 is a diagram illustrating the fourth abnormal gait criterion.

FIG. 7 is a diagram illustrating the fourth abnormal gait criterion. FIG. 7 is a schematic diagram in a case where a paralyzed body portion, which is the lower body of the affected leg side, is observed from the side with respect to the gait direction, and shows each body portion in the same manner as in FIG. 4.

In order to determine whether or not the gait of the trainee 900 meets the fourth abnormal gait criterion, the overall controller 210 detects, as a fourth motion amount according to the gait motion, a distance $X_4$ along the gait direction from the hip joint HJ to the foot joint FJ at the time of swinging at which the affected leg switches from the stance phase to the swing phase. In the gait of a healthy person, the foot joint FJ at the time of swinging is located behind the hip joint HJ to some extent. In the gait of a paralyzed patient, since the weight shift of the upper body cannot be freely performed, swinging may be started before the foot joint FJ is sufficiently separated from the hip joint HJ.

"Equal to or greater than a reference distance $X_{c4}$" is set as the fourth abnormal gait criterion. In a case where the distance $X_4$ detected in the gait motion is less than the reference distance $X_{c4}$, determination as an abnormal gait is made. The overall controller 210 acquires the detection signal from the load sensor 222 and the image data from the camera 140, and detects the distance $X_4$ at the time of swinging at which the affected leg switches from the stance phase to the swing phase using the acquired information. For example, in a case where $X_{c4}$=−20 cm (20 cm backward from the hip joint HJ) is set, the gait evaluation unit 210a evaluates the gait motion of the trainee 900 as an abnormal gait in a case where the detected distance $X_4$ is −10 cm (10 cm backward from the hip joint HJ) or 5 cm (5 cm forward from the hip joint HJ). The reference distance $X_{c4}$ may be changed according to the physique of the trainee 900, the degree of progress of rehabilitation, and the like.

Figure 8:
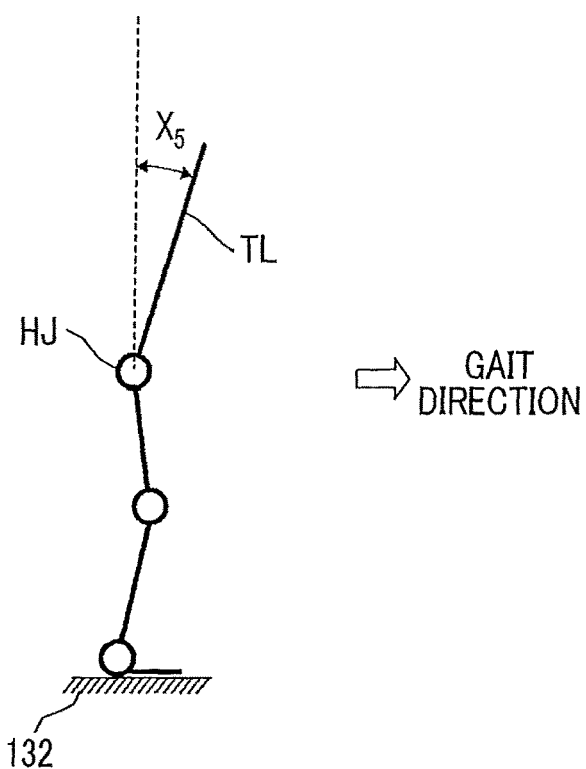
FIG. 8 is a diagram illustrating the fifth abnormal gait criterion.

FIG. 8 is a diagram illustrating the fifth abnormal gait criterion. FIG. 8 is a schematic diagram in a case where a paralyzed body portion, which is the lower body of the affected leg side, is observed from the side with respect to the gait direction, and shows each body portion in the same manner as in FIG. 4.

In order to determine whether or not the gait of the trainee 900 meets the fifth abnormal gait criterion, the overall controller 210 detects an inclination angle $X_5$ of the trunk TL in the forward direction during the stance of the affected leg as a fifth motion amount according to the gait motion. In the normal gait of a healthy person, the trunk TL during the stance is slightly inclined forward with respect to the vertical line passing through the hip joint HJ. In the gait of a paralyzed patient, in order to try to protect the lower body, the trunk TL may be greatly inclined forward with respect to the vertical line passing through the hip joint HJ.

"Equal to or greater than a reference angle $X_{c5}$" is set as the fifth abnormal gait criterion. In a case where the inclination angle $X_5$ in the forward direction detected in the gait motion is equal to or greater than the reference angle $X_{c5}$, determination as an abnormal gait is made. The overall controller 210 acquires the detection signal from the posture sensor 217 and the image data from the camera 140, and detects the inclination angle $X_5$ during the stance using the acquired information. For example, in a case where $X_{c5}=10°$ is set, the gait evaluation unit 210a evaluates the gait motion of the trainee 900 as an abnormal gait in a case where the detected inclination angle $X_5$ is 30°. The gait evaluation unit 210a evaluates the gait motion of the trainee 900 as an abnormal gait in a case where the inclination angle $X_5$ continuously detected during the stance is equal to or greater than the reference angle $X_{c5}$ at least once. The reference angle $X_{c5}$ may be changed according to the age of the trainee 900, the degree of progress of rehabilitation, and the like.

Figure 9:
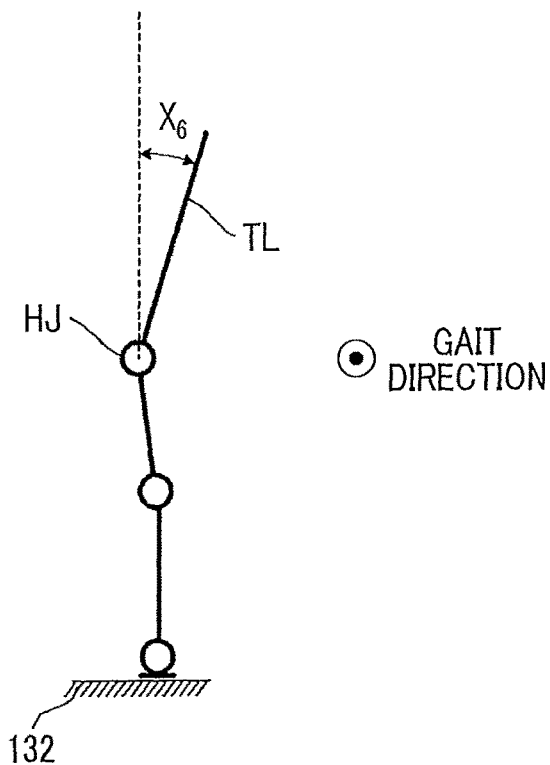
FIG. 9 is a diagram illustrating the sixth abnormal gait criterion.

FIG. 9 is a diagram illustrating the sixth abnormal gait criterion. FIG. 9 is a schematic diagram in a case where a paralyzed body portion, which is the lower body of the affected leg side, is observed from the front in the gait direction, and shows each body portion in the same manner as in FIG. 4.

In order to determine whether or not the gait of the trainee 900 meets the sixth abnormal gait criterion, the overall controller 210 detects an inclination angle $X_6$ of the trunk TL toward the affected leg side during the stance of the affected leg as a sixth motion amount according to the gait motion. In the normal gait of a healthy person, the trunk TL during the stance is rarely shaken in the right and left direction with respect to the vertical line passing through the hip joint HJ. In the gait of a paralyzed patient, the trunk TL may be greatly inclined forward toward the affected leg side with respect to the vertical line passing through the hip joint HJ due to the fear of applying weight to the affected leg side and the like.

"Equal to or greater than a reference angle $X_{c6}$" is set as the sixth abnormal gait criterion. In a case where the inclination angle $X_6$ toward the affected leg side detected in the gait motion is equal to or greater than the reference angle $X_{c6}$, determination as an abnormal gait is made. The overall controller 210 acquires the detection signal from the posture sensor 217 and the image data from the camera 140, and detects the inclination angle $X_6$ during the stance using the acquired information. For example, in a case where $X_{c6}=10°$ is set, the gait evaluation unit 210a evaluates the gait motion of the trainee 900 as an abnormal gait in a case where the detected inclination angle $X_6$ is 20°. The gait evaluation unit 210a evaluates the gait motion of the trainee 900 as an abnormal gait in a case where the inclination angle $X_6$ continuously detected during the stance is equal to or greater than the reference angle $X_{c6}$ at least once. The reference angle $X_{c6}$ may be changed according to the age of the trainee 900, the degree of progress of rehabilitation, and the like.

Figure 10:
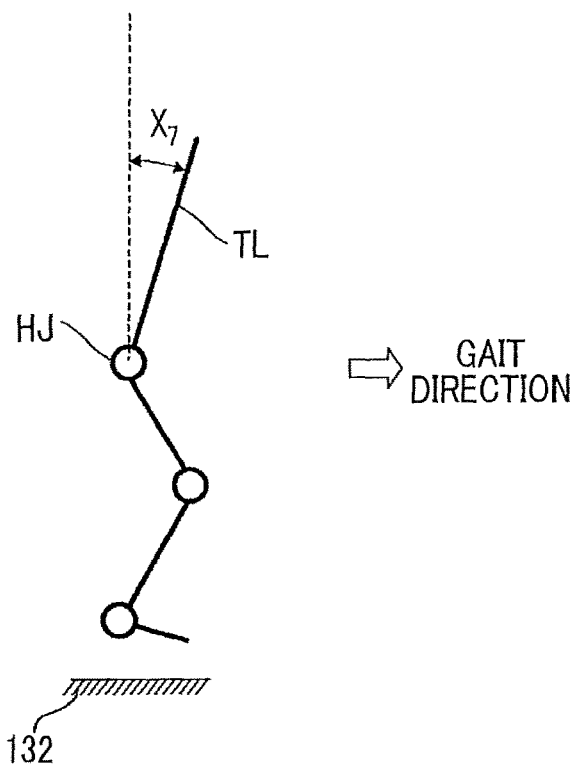
FIG. 10 is a diagram illustrating the seventh abnormal gait criterion.

FIG. 10 is a diagram illustrating the seventh abnormal gait criterion. FIG. 10 is a schematic diagram in a case where a paralyzed body portion, which is the lower body of the affected leg side, is observed from the side with respect to the gait direction, and shows each body portion in the same manner as in FIG. 4.

In order to determine whether or not the gait of the trainee 900 meets the seventh abnormal gait criterion, the overall controller 210 detects an inclination angle $X_7$ of the trunk TL in the forward direction during the swing of the affected leg as a seventh motion amount according to the gait motion. In the normal gait of a healthy person, the trunk TL during the swing is inclined forward to some extent with respect to the vertical line passing through the hip joint HJ. In the gait of a paralyzed patient, since the weight shift of the upper body cannot be freely performed and accordingly the upper body is bent backward, the trunk TL may be inclined backward with respect to the vertical line passing through the hip joint HJ.

"Less than a reference angle $X_{c7}$" is set as the seventh abnormal gait criterion. In a case where the inclination angle $X_7$ in the forward direction detected in the gait motion is less than the reference angle $X_{c7}$, determination as an abnormal gait is made. The overall controller 210 acquires the detection signal from the posture sensor 217 and the image data from the camera 140, and detects the inclination angle $X_7$ during the swing using the acquired information. For example, in a case where $X_{c7}=-5°$ (=5° backward) is set, the gait evaluation unit 210a evaluates the gait motion of the trainee 900 as an abnormal gait in a case where the detected inclination angle $X_7$ is −20°. The gait evaluation unit 210a evaluates the gait motion of the trainee 900 as an abnormal gait in a case where the inclination angle $X_7$ continuously detected during the swing is less than the reference angle $X_{c7}$ at least once. The reference angle $X_{c7}$ may be changed according to the age of the trainee 900, the degree of progress of rehabilitation, and the like.

Although the seven abnormal gait criteria have been described as described above, other abnormal gait criteria may be added. In defining abnormal gait criteria, it is needed to define a plurality of abnormal gait criteria rather than one abnormal gait criterion. In this case, at least two or more abnormal gait criteria relevant to the motion amounts of different parts of the paralyzed body portion may be included, or at least two or more abnormal gait criteria relevant to the motion amount of the same part of the paralyzed body portion in different directions may be included.

Two or more criteria relevant to the motion amounts of different parts may be selected from criteria relevant to the motion amount of the trunk, criteria relevant to the motion amount of the knee joint, and criteria relevant to the motion amount of the foot portion from the ankle. In the embodiment described above, the criteria relevant to the motion amount of the trunk are the fifth, sixth, and seventh criteria, the criteria relevant to the motion amount of the knee joint are the third criterion, and the criteria relevant to the motion amount of the foot portion are the first, second, and fourth criteria. In a case where a motion amount of interest is selected as described above, it has become obvious through experiments that, in a case where the actual gait should be evaluated as an abnormal gait, the actual gait is not evaluated as an abnormal gait from one motion amount and is evaluated as an abnormal gait from another motion amount in many cases.

Two or more criteria relevant to the motion amount of the same part of the paralyzed body portion in different directions may include a criterion relevant to the motion amount of the trunk in the gait direction and a criterion relevant to the motion amount of the trunk in an orthogonal direction perpendicular to the gait direction. In the embodiment described above, the relationship between any one of the fifth and seventh criteria and the sixth criterion corresponds thereto. Also in a case where motion amounts of interest are combined as described above, it has become obvious through experiments that, in a case where the actual gait should be evaluated as an abnormal gait, the actual gait is not evaluated as an abnormal gait from one motion amount and is evaluated as an abnormal gait from another motion amount in many cases.

It can be seen that abnormal gait criteria may be set to different criteria in the swing phase and the stance phase of the affected leg. The first criterion and the fourth criterion are criteria of the same part in the same direction. However, the first criterion and the fourth criterion are focused on the time point of switching from the swing phase to the stance phase and the time point of switching from the stance phase to the swing phase, respectively. Similarly, the fifth criterion and the seventh criterion are criteria of the same part in the same direction. However, the fifth criterion and the seventh criterion are focused on the stance phase and the swing phase, respectively. Even the motion amounts of the same part in the same direction can be evaluated as different feature amounts of the gait motion in a case where the observation time point can be distinguished.

Figure 11:
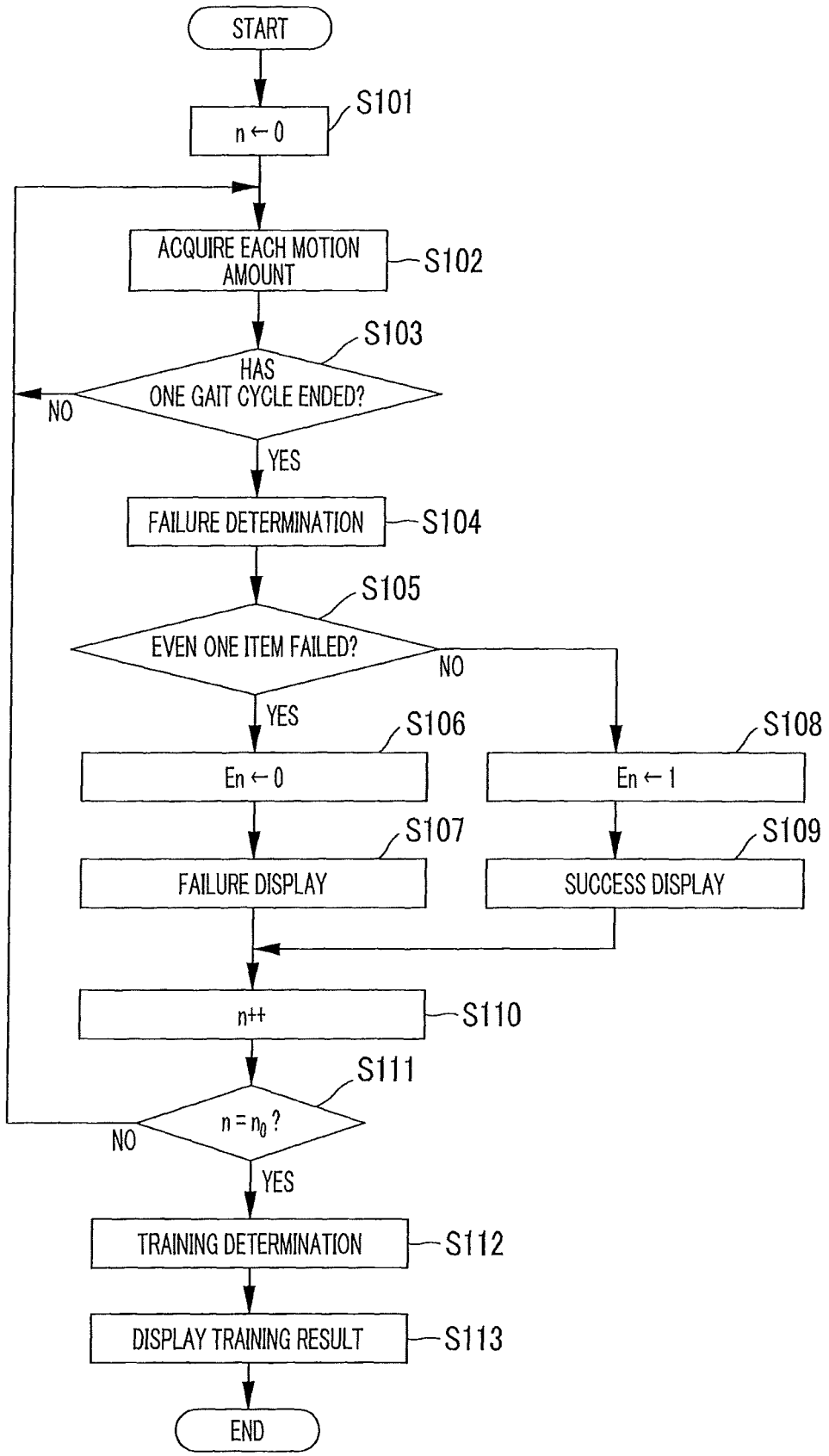
FIG. 11 is a flowchart showing the processing operation of the gait training apparatus.

The processing operation of the gait training apparatus 100 will be described. FIG. 11 is a flowchart showing the processing operation of the gait training apparatus. The flow starts at a point in time at which a series of training programs are activated in a case where a training menu is selected by the trainee 900 or the operator.

In step S101, the overall controller 210 resets a gait cycle counter n. The overall controller 210 drives the treadmill driving unit 211 to start the rotation of the belt 132, and drives the tension driving unit 214 and the joint driving unit 221 according to the set adjustment value to assist the gait of the trainee 900. In a case where the trainee 900 starts a gait motion, each motion amount according to the gait motion is acquired in step S102. Specifically, the image processor 216 analyzes the image signal acquired from the camera 140, or the detection signals from the posture sensor 217, the load sensor 222, and the angle sensor 223 are acquired and converted into the motion amount.

In step S103, the overall controller 210 determines whether or not one gait cycle has ended. Evaluation of an abnormal gait may be performed for each step of the affected leg. In the present embodiment, however, evaluation is performed in one cycle of one step of the affected leg and one step of the healthy leg subsequent to the one step of the affected leg. Accordingly, in a case where the overall controller 210 determines that one gait cycle has ended, the overall controller 210 proceeds to step S104 to execute evaluation. In a case where the overall controller 210 determines that one gait cycle has not ended, the overall controller 210 returns to step S102 to continue the acquisition of each motion amount.

In step S104, the gait evaluation unit 210a of the overall controller 210 evaluates an abnormal gait. Specifically, the gait evaluation unit 210a totals the motion amounts of respective parts in each direction and each period in the gait motion to check whether or not the totaled amount meets each of the abnormal gait criteria. In a case where the gait motion of the trainee 900 is evaluated as an abnormal gait, the gait evaluation unit 210a determines the gait motion of the trainee 900 as a failed gait. In step S105, the gait evaluation unit 210a determines whether or not the totaled amount meets one of the abnormal gait criteria described above. In a case where the gait evaluation unit 210a determines that the totaled amount meets one of the abnormal gait criteria described above, the gait evaluation unit 210a proceeds to step S106 to substitute "0" into an evaluation variable En of the n-th step. The overall controller 210 displays the fact that the one step is a failed gait on the training monitor 138 and the management monitor 139 through the display controller 213. In a case where the gait evaluation unit 210a determines that the totaled amount does not meet any of the abnormal gait criteria described above in step S105, the gait evaluation unit 210a proceeds to step S108 to substitute "1" into the evaluation variable En of the n-th step. The overall controller 210 displays the fact that the one step is successful gait on the training monitor 138 and the management monitor 139 through the display controller 213.

In the case of displaying the failed gait in real time during training, it is desirable to perform simple and single display without indicating which of the abnormal gait criteria the gait motion of the trainee 900 meets although the disclosure is not particularly limited thereto. In the case of presenting the gait motion of the trainee 900 as a failed gait by simple and single display, the trainee 900 can recognize the minimum situation of the trainee 900 himself or herself without being confused during the gait training. Means for presenting whether or not the gait motion of the trainee 900 is a failed gait is not limited to the management monitor 139, and a buzzer sound, blinking light, and the like can be used. Also in this case, although not particularly limited, it is desirable to show the sound or light to the trainee 900 in a simple and single manner. The management monitor 139 for presenting the fact that the gait motion of the trainee 900 is a failed gait as described above, a device for generating sound or light, and the like function as presentation units for presenting information regarding the evaluation of the gait evaluation unit 210a.

After ending the failure display in step S107 or the success display in step S109, the overall controller 210 proceeds to step S110 to increment the gait cycle counter n. In step S111, the overall controller 210 determines whether or not the gait cycle counter n has reached a gait cycle number $n_0$ scheduled in a series of gait training programs. In a case where the overall controller 210 determines that the gait cycle counter n has not reached the gait cycle number no, the overall controller 210 returns to step S102 to continue the gait training control. In a case where the overall controller 210 determines that the gait cycle counter n has reached the gait cycle number n0, the overall controller 210 proceeds to step S112.

In step S112, the training determination unit 210b of the overall controller 210 totals the evaluation results in a series of gait training trials performed continuously, and performs determination to indicate the success degree of the gait training trial. Specifically, the training determination unit 210b derives a training determination by calculating the ratio of the number of failed gaits to the total number of gaits of the affected leg or by evaluating the number of fall avoiding operations by which the harness driving unit 215 has been operated. The overall controller 210 ends the series of processes after the training determination unit 210*b* displays the determination result on the training monitor 138 and the management monitor 139 through the display controller 213 in step S113.

Figure 12:
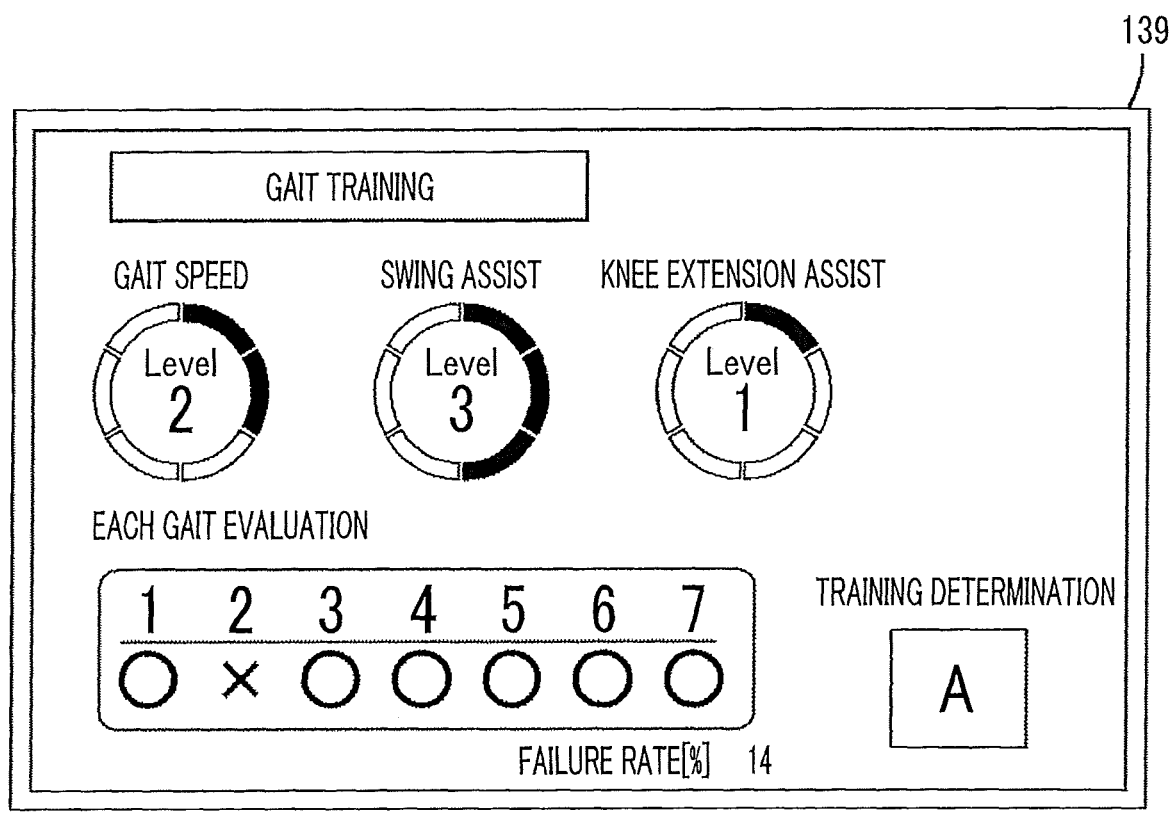
FIG. 12 is a display example showing a determination result.

FIG. 12 is a display example showing a determination result on the management monitor 139. The gait speed, the swing assist, and the knee extension assist are parameters that are set as levels according to the level of difficulty of the training menu. The gait speed is proportional to the speed at which the belt 132 of the treadmill 131 is rotated. In the initial stage of training, the gait speed is set to be low. The swing assist is proportional to the assisting force to assist the swing of the affected leg by winding and unwinding the front side wire 134 and the rear side wire 136. In the final stage of training, the front side wire 134 and the rear side wire 136 are pulled with a driving force enough to offset the weight of the gait assistance device 120. The knee extension assist is proportional to the driving torque of the joint driving unit. In a situation in which knee folding is likely to occur in the affected leg, assistance is steadily performed.

Each gait evaluation indicates the evaluation result of each gait cycle, for example, O indicates success and X indicates failure. In the display example shown in FIG. 12, it can be seen that, in the gait cycle of seven steps in one training, the second step is a failure and the failure rate as a whole is 14%. The training determination performed by the training determination unit 210*b* is displayed as "A" determination, for example.

Since the gait training apparatus 100 according to the present embodiment includes the harness wire 111 and the like as a falling prevention device that prevents falling on the treadmill 131, the trainee 900 can continue gait training even in a case where the trainee 900 is about to lose his or her posture. Therefore, it is possible to comprehensively determine the degree of normality for continuous gait needed as a normal gait motion.

In particular, in a case where a patient suffering from paralysis in the leg does gait training as a rehabilitation, doing the gait training with the level of difficulty at which gait is barely performed, that is, the level of difficulty at which the trainee loses his or her posture to some extent, increases the training effect (so-called exercise learning effect). In the related art, since a therapist checks the training situation of a patient and adjusts the setting of the level of difficulty of the next session, the recovery effect of the patient depends on the experience and intuition of the therapist. Since the gait training apparatus 100 according to the present embodiment can perform objective training determination, even a therapist with little experience can easily determine the level of difficulty of the next training session. Therefore, it can be expected that the training effect of the patient will be improved.

Figure 13:
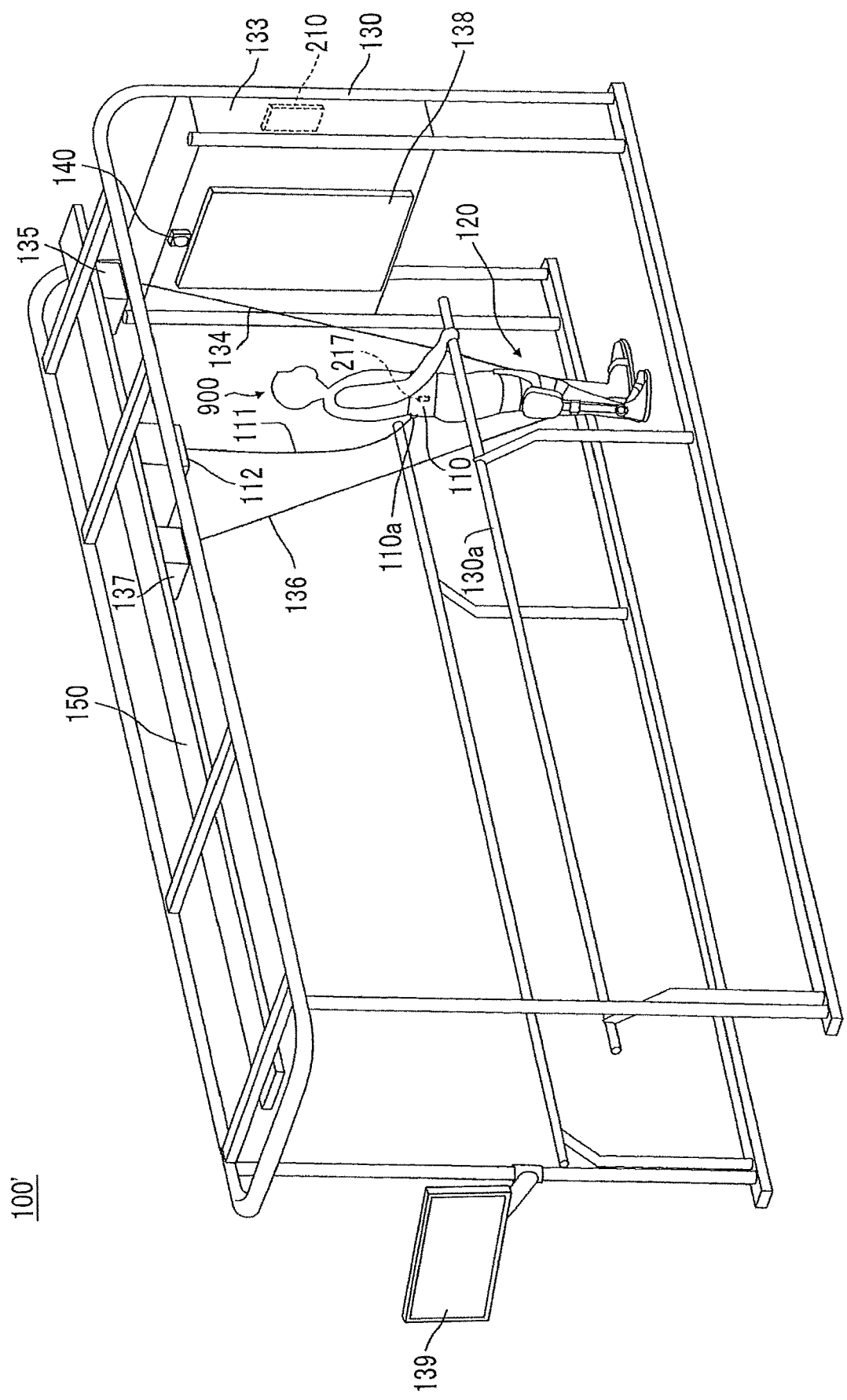
FIG. 13 is a schematic perspective view of a gait training apparatus according to a modification example.

A modification example of the gait training apparatus 100 will be described. FIG. 13 is a schematic perspective view of a gait training apparatus 100' according to a modification example. The gait training apparatus 100' is different from the gait training apparatus 100 described above in that the treadmill 131 is not provided and the trainee 900 actually moves in the space surrounded by the frame 130. In FIG. 13, elements common to the gait training apparatus 100 are denoted by the same reference numerals, and the description thereof will be omitted.

The gait training apparatus 100' includes a guide rail 150 for guiding the harness pulling unit 112, the front side pulling unit 135, and the rear side pulling unit 137. The harness pulling unit 112, the front side pulling unit 135, and the rear side pulling unit 137 move along the guide rail by a motor (not shown). The overall controller 210 determines the gait position of the trainee 900, and arranges the harness pulling unit 112, the front side pulling unit 135, and the rear side pulling unit 137 at the optimal positions according to the determined gait position. In the gait training apparatus 100' configured as described above, since the trainee 900 actually moves relative to the floor surface, a sense of accomplishment of rehabilitation training can be obtained more.

In the embodiment described above, in a case where the trainee 900 does training next time, the gait training apparatuses 100, 100' may set parameters, such as a swing assist level, according to the previous training determination. Since the gait training apparatus adjusts the training intensity automatically as described above, the burden on the operator is reduced. The gait training apparatuses 100 and 100' may adjust the gait speed and the like dynamically according to the evaluation of each step during the training. For example, in a case where the evaluation indicating an abnormal gait continues, the gait speed may be reduced. By the dynamic control described above, the safety of the trainee 900 can be secured, and the level of difficulty can be adjusted according to his or her ability.

In the embodiment described above, an example has been described in which the trainee 900 is a hemiplegic patient suffering from paralysis in one of the legs. However, the gait training apparatuses 100, 100' may also be applied to a patient suffering from paralysis in both legs. In this case, training is performed by attaching the gait assistance device 120 to both legs. In this case, the evaluation of an abnormal gait may be performed for each of the affected legs. The degree of recovery of each affected leg can be individually determined by performing the evaluation of an abnormal gait independently for each affected leg.

The embodiment described above is just an example for carrying out the disclosure. Therefore, the disclosure is not limited thereto, and can be appropriately changed and executed within the scope of the disclosure described in the claims.

What is claimed is:

1. A gait training apparatus for training a gait of a paralyzed patient suffering from paralysis in an affected leg, the gait training apparatus comprising:
   a gait assistance device configured to be attached to the affected leg, the gait assistance device including an actuator configured to control a motion of the affected leg, an upper leg frame, a lower leg frame rotatably connected to the upper leg frame, a foot frame rotatably connected to the lower leg frame, an angle sensor measuring an angle formed by the upper leg frame and the lower leg frame around a hinge axis, and a load sensor being disposed in the foot frame and measuring a vertical load applied to a sole of the patient;
   a treadmill that serves as a gait surface on which the patient walks;
   a frame, a top of the frame supporting a front side pulling unit, a rear side pulling device, and a harness pulling unit, the front side pulling unit including a front side wire connected to a front side of the gait assistance device, the rear side pulling device including a rear side wire connected to a rear side of the gait assistance device, and the harness pulling unit including a harness wire connected to a harness attached to the patient to prevent the patient from falling on the treadmill;
   a display device mounted on the frame; and
   a controller including processing circuitry configured to:

acquire, according to a gait motion, a plurality of motion amounts of a paralyzed body portion, which includes the affected leg, the plurality of motion amounts obtained from image data received from a camera, a posture sensor provided on the patient, and the load sensor and the angle sensor provided on a gait assistance device, evaluate that the gait motion is an abnormal gait in a case where at least one of the motion amounts from the plurality of motion amounts meets any one of a plurality of abnormal gait criteria set in advance for a trial in which the patient continuously walks on the treadmill, transmit, to the display device, a display signal that causes the display device to display a determination result indicating whether the gait motion is the abnormal gait, wherein the processing circuitry of the controller is further configured to operate the front side pulling unit and the rear side pulling unit according to movement of the affected leg, and operate the harness pulling unit based on movement of the patient, wherein the abnormal gait criteria are set to different criteria in a swing phase and a stance phase of the affected leg, and wherein the abnormal gait criteria include at least two or more first criteria, which are criteria relevant to motion amounts of different parts of the paralyzed body portion, the first criteria being selected from a criterion relevant to a motion amount of a trunk, a criterion relevant to a motion amount of a knee joint, and a criterion relevant to a motion amount of a foot portion from an ankle, or at least two second criteria, which are criteria relevant to motion amounts of the same part of the paralyzed body portion in different directions, the second criteria including a criterion relevant to a motion amount of a trunk in a gait direction and a criterion relevant to a motion amount of the trunk in an orthogonal direction perpendicular to the gait direction, wherein the criterion relevant to the motion amount of the trunk, the criterion relevant to the motion amount of the trunk in the gait direction, and the criterion relevant to the motion amount of the trunk in the orthogonal direction perpendicular to the gait direction are each based on at least one of an inclination angle of the trunk of a forward direction during a stance of the affected leg being equal to or greater than a first predetermined reference angle, an inclination angle of the trunk toward a side of the affected leg during the stance of the affected leg being equal to or greater than a second predetermined reference angle, and an inclination angle of the trunk in the forward direction during a swing of the affected leg being equal to or greater than a third predetermined reference angle, wherein the criterion relevant to the motion amount of the knee joint is based on a bending angle of the knee joint during the stance of the affected leg being less than a fourth predetermined reference angle, and wherein the criterion relevant to the motion amount of the foot portion from the ankle is based on at least one of a distance along the gait direction from a hip joint to a foot joint when the affected leg has finished the swing phase and landed is less than a first predetermined reference distance, the vertical load applied to the sole of the patient is larger than a predetermined reference load, and a distance along the gait direction from the hip joint to the foot joint at a time of swinging at which the affected leg switches from the stance phase to the swing phase is equal to or greater than a second predetermined reference distance.

2. The gait training apparatus according to claim 1, wherein:
the paralyzed patient is a hemiplegic patient suffering from paralysis in the affected leg; and
the processing circuitry is further configured to evaluate the abnormal gait for at least one of each step of the affected leg or one cycle including one step of the affected leg and one step of a healthy leg not suffering from paralysis.

3. The gait training system according to claim 1, wherein the display device performs a single abnormality presentation even in a case where each of the motion amounts meets any one of the abnormal gait criteria.

4. A gait evaluation method performed by a gait training apparatus for evaluating a training gait of a paralyzed patient suffering from paralysis in an affected leg, the gait evaluation method comprising:
providing the gait training apparatus including
a gait assistance device configured to be attached to the affected leg, the gait assistance device including an actuator configured to control a motion of the affected leg, an upper leg frame, a lower leg frame rotatably connected to the upper leg frame, a foot frame rotatably connected to the lower leg frame, an angle sensor measuring an angle formed by the upper leg frame and the lower leg frame around a hinge axis, and a load sensor being disposed in the foot frame and measuring a vertical load applied to a sole of the patient;
a treadmill that serves as a gait surface on which the patient walks;
a frame, a top of the frame supporting a front side pulling unit, a rear side pulling device, and a harness pulling unit, the front side pulling unit including a front side wire connected to a front side of the gait assistance device, the rear side pulling device including a rear side wire connected to a rear side of the gait assistance device, and the harness pulling unit including a harness wire connected to a harness attached to the patient to prevent the patient from falling on the treadmill; and
a display device mounted on the frame
acquiring, according to a gait motion, a plurality of motion amounts of a paralyzed body portion, which includes the affected leg, the plurality of motion amounts obtained from image data received from a camera, a posture sensor provided on the patient, and the load sensor and the angle sensor provided on the gait assistance device,
evaluating that the gait motion is an abnormal gait in a case where at least one of the motion amounts from the plurality of motion amounts meets any one of a plurality of abnormal gait criteria set in advance for a trial in which the patent continuously walks on the treadmill,
transmitting, to the display device, a display signal that causes the display device to display a determination result indicating whether the gait motion is the abnormal gait, and
operating the front side pulling unit and the rear side pulling unit according to movement of the affected leg, and operating the harness pulling unit based on movement of the patient wherein the abnormal gait criteria are set to different criteria in a swing phase and a stance phase of the affected leg, and wherein the abnormal gait criteria include at least two or more first criteria, which are criteria relevant to motion amounts of different parts of the paralyzed body portion, the first criteria being selected from a criterion relevant to a motion amount of a trunk, a criterion relevant to a motion amount of a knee joint, and a criterion relevant to a motion amount of a foot portion from an ankle, or at least two second criteria, which are criteria relevant to motion amounts of the same part of the paralyzed body portion in different directions, the second criteria including a criterion relevant to a motion amount of a trunk in a gait direction and a criterion relevant to a motion amount of the trunk in an orthogonal direction perpendicular to the gait direction, wherein the criterion relevant to the motion amount of the trunk, the criterion relevant to the motion amount of the trunk in the gait direction, and the criterion relevant to the motion amount of the trunk in the orthogonal direction perpendicular to the gait direction are each based on at least one of an inclination angle of the trunk of a forward direction during a stance of the affected leg being equal to or greater than a first predetermined reference angle, an inclination angle of the trunk toward a side of the affected leg during the stance of the affected leg being equal to or greater than a second predetermined reference angle, and an inclination angle of the trunk in the forward direction during a swing of the affected leg being equal to or greater than a third predetermined reference angle, wherein the criterion relevant to the motion amount of the knee joint is based on a bending angle of the knee joint during the stance of the affected leg being less than a fourth predetermined reference angle, and wherein the criterion relevant to the motion amount of the foot portion from the ankle is based on at least one of a distance along the gait direction from a hip joint to a foot joint when the affected leg has finished the swing phase and landed is less than a first predetermined reference distance, the vertical load applied to the sole of the patient is larger than a predetermined reference load, and a distance along the gait direction from the hip joint to the foot joint at a time of swinging at which the affected leg switches from the stance phase to the swing phase is equal to or greater than a second predetermined reference distance.

5. A gait training apparatus for training a gait of a paralyzed patient suffering from paralysis in an affected leg, the gait training apparatus comprising:

a gait assistance device configured to be attached to the affected leg, the gait assistance device including an actuator configured to control a motion of the affected leg, an upper leg frame, a lower leg frame rotatably connected to the upper leg frame, a foot frame rotatably connected to the lower leg frame, an angle sensor measuring an angle formed by the upper leg frame and the lower leg frame around a hinge axis, and a load sensor being disposed in the foot frame and measuring a vertical load applied to a sole of the patient;

a frame surrounding a gait surface on which the patient walks, a top of the frame supporting a front side pulling unit, a rear side pulling device, and a harness pulling unit, the front side pulling unit including a front side wire connected to a front side of the gait assistance device, the rear side pulling device including a rear side wire connected to a rear side of the gait assistance device, and the harness pulling unit including a harness wire connected to a harness attached to the patient to prevent the patient from falling;

a display device mounted on the frame; and a controller including processing circuitry configured to:
acquire, according to a gait motion, a plurality of motion amounts of a paralyzed body portion, which includes the affected leg, the plurality of motion amounts obtained from image data received from a camera, a posture sensor provided on the patient, and the load sensor and the angle sensor provided on a gait assistance device, evaluate that the gait motion is an abnormal gait in a case where at least one of the motion amounts from the plurality of motion amounts meets any one of a plurality of abnormal gait criteria set in advance for a trial in which the patient continuously walks on the gait surface, transmit, to the display device, a display signal that causes the display device to display a determination result indicating whether the gait motion is the abnormal gait, wherein the processing circuitry of the controller is further configured to operate the front side pulling unit and the rear side pulling unit according to movement of the affected leg, and operate the harness pulling unit based on movement of the patient, wherein the abnormal gait criteria are set to different criteria in a swing phase and a stance phase of the affected leg, and wherein the abnormal gait criteria include at least two first criteria, which are criteria relevant to motion amounts of different parts of the paralyzed body portion, the first criteria being selected from a criterion relevant to a motion amount of a trunk, a criterion relevant to a motion amount of a knee joint, and a criterion relevant to a motion amount of a foot portion from an ankle, or at least two second criteria, which are criteria relevant to motion amounts of the same part of the paralyzed body portion in different directions, the second criteria including a criterion relevant to a motion amount of a trunk in a gait direction and a criterion relevant to a motion amount of the trunk in an orthogonal direction perpendicular to the gait direction, wherein the criterion relevant to the motion amount of the trunk, the criterion relevant to the motion amount of the trunk in the gait direction, and the criterion relevant to the motion amount of the trunk in the orthogonal direction perpendicular to the gait direction are each based on at least one of an inclination angle of the trunk of a forward direction during a stance of the affected leg being equal to or greater than a first predetermined reference angle, an inclination angle of the trunk toward a side of the affected leg during the stance of the affected leg being equal to or greater than a second predetermined reference angle, and an inclination angle of the trunk in the forward direction during a swing of the affected leg being equal to or greater than a third predetermined reference angle, wherein the criterion relevant to the motion amount of the knee joint is based on a bending angle of the knee joint during the stance of the affected leg being less than a fourth predetermined reference angle, and wherein the criterion relevant to the motion amount of the foot portion from the ankle is based on at least one of a distance along the gait direction from a hip joint to a foot joint when the affected leg has finished the swing phase and landed is less than a first predetermined reference distance, the vertical load applied to the sole of the patient is larger than a predetermined reference load, and a distance along the gait direction from the hip joint to the foot joint at a time of swinging at which the affected leg switches from the stance phase to the swing phase is equal to or greater than a second predetermined reference distance.

* * * * *